(12) United States Patent
Goodridge

(10) Patent No.: US 10,072,307 B1
(45) Date of Patent: Sep. 11, 2018

(54) ISOLATION OF VIRUSES USING ANIONIC RESIN BEADS

(75) Inventor: Lawrence D. Goodridge, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 1132 days.

(21) Appl. No.: 12/693,139

(22) Filed: Jan. 25, 2010

Related U.S. Application Data

(60) Provisional application No. 61/146,951, filed on Jan. 23, 2009.

(51) Int. Cl.
*C12Q 1/70* (2006.01)

(52) U.S. Cl.
CPC .................................... *C12Q 1/70* (2013.01)

(58) Field of Classification Search
None
See application file for complete search history.

(56) References Cited

U.S. PATENT DOCUMENTS

| | | | |
|---|---|---|---|
| 4,246,101 | A | 1/1981 | Selby, III |
| 5,192,551 | A | 3/1993 | Willoughby, Jr. et al. |
| 7,494,771 | B2 | 2/2009 | Picard et al. |
| 7,611,831 | B2 | 11/2009 | Hei |
| 2005/0112752 | A1 | 5/2005 | Polo et al. |
| 2007/0292937 | A1 | 12/2007 | Pernthaler et al. |
| 2009/0042274 | A1 | 2/2009 | Ioka |

OTHER PUBLICATIONS

Deponte et al., Anal Bioanal Chem, 2004, 379:419-426.*
Rodrigues et al., Journal of Chromatography B, 2006, 837:59-68.*
Nishikubo et al., Journal of Organic Chemistry, 1990, 55:2536-2542.*
Desai et al., Applied and Environmental Microbiology, Apr. 2008, 74(7):2254-2258.*
Sakudo et al., Biochemical and Biophysical Research Communications, Sep. 28, 2008, 377:85-88.*
World Health Organization: INFOSAN Information Note No. Jul. 2005—Avian Influenza.*
Atmar et al., Diagnosis of Noncultivatable Gastroenteritis Viruses, the Human Caliciviruses, Clinical Microbiology Reviews, 2001, vol. 14, No. 1, pp. 15-37.
Bae et al., Evaluation of Murine Norovirus, Feline Calicivirus, Poliovirus, and MS2 as Surrogates for Human Norovirus in a Model of Viral Persistence in Surface Water and Groundwater, Applied and Environmental Microbiology, 2008, vol. 74, No. 2, pp. 477-484.
Cornejo et al., Comparison of C18-Carboxypropylbetaine and Glass Bead DNA Extraction Methods for Detection of *Mycobacterium bovis* in Bovine Milk Samples and Analysis of Samples by PCR, Applied and Environmental Microbiology, 1998, vol. 64, No. 8, pp. 3099-3101.

Dore et al., Evaluation of F-Specific RNA Bacteriophage as a Candidate Human Enteric Virus Indicator for Bivalve Molluscan Shellfish, Applied and Environmental Microbiology, 2000, vol. 66, No. 4, pp. 1280-1285.
Fout et al., A Multiplex Reverse Transcription—PCR Method for Detection of Human Enteric Viruses in Groundwater, Applied and Environmental Microbiology, 2003, vol. 69, No. 6, pp. 3158-3164.
Leclerc et al., Bacteriophages as Indicators of Enteric Viruses and Public Health Risk in Groundwaters, Journal of Applied Microbiology, 2000, vol. 88, pp. 5-21.
Lodder et al., Presence of Noroviruses and Other Enteric Viruses in Sewage and Surface Waters in the Netherlands, Applied and Environmental Microbiology, 2005, vol. 71, No. 3, pp. 1453-1461.
Koopmans et al., Foodborne Viruses: An Emerging Problem, International Journal of Food Microbiology, 2004, vol. 90, pp. 23-41.
Green et al., Comparative Detection of Enteric Viruses in Wastewaters, Sediments and Oysters by Reverse Transcription—PCR and Cell Culture, Water Research, 1999, vol. 33, No. 5, pp. 1195-1200.
Simmons III et al., Concentration and Detection of Cryptosporidium Oocysts in Surface Water Samples by Method 1622 Using Ultrafiltration and Capsule Filtration, Applied and Environmental Microbiology, 2001, vol. 67, No. 3, pp. 1123-1127.
Lee et al., Detection of Infectious Enteroviruses and Adenoviruses in Tap Water in Urban Areas in Korea, Water Research, 2002, vol. 36, pp. 248-256.
Puig et al., Detection of Adenoviruses and Enteroviruses in Polluted Waters by Nested PCR Amplification, Applied and Environmental Microbiology, 1994, vol. 60, No. 8, pp. 2963-2970.
Myrmel et al., Detection of Small Round Structured Viruses in Artificially Contaminated Water Using Filter Adsorption and Reverse Transcription Polymerase Chain Reaction, International Journal of Food Microbiology, 1999, vol. 49, pp. 85-94.
Jiang et al., PCR Detection of Pathogenic Viruses in Southern California Urban Rivers, Journal of Applied Microbiology, 2004, vol. 97, pp. 17-28.
Enriquez et al., Concentration of Enteric Adenovirus 40 From Tap, Sea and Waste Water, Water Research, 1995, vol. 29, No. 11, pp. 2554-2560.

* cited by examiner

*Primary Examiner* — Nicole Kinsey White
(74) *Attorney, Agent, or Firm* — Michael M. McGaw; Smith & Hopen P.A.

(57) ABSTRACT

An isolation and detection method for viruses from large quantities of water or other aqueous media. The technology employs charged resins to isolate viral particles from liquid sources such as water, milk, juices, and homogenized food. Anionic resin beads are added to a sample liquid and suspended within the liquid. While in suspension the anionic beads complex with negatively charged virus particles of other pathogens. The complexed beads are then removed from the liquid, effecting the isolation of the virus. Detection techniques can then be performed directly on the complexed beads without resorting to additional steps to elute the virus or other pathogen from the bead. The methodology can be employed for the detection of bacteriophage in an aqueous medium where the bacteriophage serves as a surrogate for the presence of a pathogen or other contaminant, such as an enteric virus.

23 Claims, 6 Drawing Sheets

ISOLATION OF VIRUSES USING ANIONIC RESIN BEADS

CROSS REFERENCE TO RELATED APPLICATIONS

This application claims priority to U.S. Provisional Patent Application 61/146,951, entitled, "Isolation and Identification of Pathogens Using Charged Resins From Large Volumes of Liquid", filed Jan. 23, 2009, the contents of which are herein incorporated by reference.

FIELD OF INVENTION

This invention relates to pathogen isolation and identification. More specifically, this invention relates to isolation of pathogens from large volumes of liquids using charged resins.

BACKGROUND OF THE INVENTION

Drinking water can become contaminated with enteric viruses and pose a significant health risk to people. These viruses enter source waterways through the direct or indirect discharge of treated and untreated human and animal waste into rivers, streams and estuaries. In general, waterborne human enteric viruses pose a greater health risk than enteric bacteria due to the low infectious dose, which may be as little as one virion [Girones, R, et al., *Wat. Sci. Technol.* (1993) 27, 235-241].

Waterborne enteric viruses replicate in the gastrointestinal tract and are shed in the feces of infected individuals. Most enteric viruses are morphologically similar, and consist of an icosahedral-shaped, non-enveloped capsid, which surrounds a single-stranded RNA (e.g. Norwalk-like virus) or double stranded DNA (e.g. adenovirus) molecule. Noroviruses and Hepatitis A are the most common enteric viruses transmitted by water [Koopmans M, and Duizer E., *Int J Food Microbiol.* (2004) 90(1):23-41]. Other common waterborne viruses include rotaviruses, echoviruses, coxsackieviruses and adenoviruses. Several of these viruses can be found on the Drinking Water Contaminant Candidate List as issued by the Environmental Protection Agency.

SUMMARY OF INVENTION

The present invention provides an isolation and detection method for viruses and other pathogens from large quantities of water or other aqueous media. The technology employs charged resins to isolate viral particles from liquid sources such as water, milk, juices, and homogenized food. Anionic resin beads are added to a sample liquid and suspended within the liquid. While in suspension the anionic beads complex with negatively charged virus particles or other pathogens. The complexed beads are then removed from the liquid, effecting the isolation of the virus. Detection techniques can then be performed directly on the complexed beads without resorting to additional steps to elute the virus or other pathogen from the bead. The methodology can be employed for the detection of bacteriophages in an aqueous medium where the bacteriophage serves as a surrogate for the presence of a pathogen or other contaminant, such as an enteric virus, or as an indicator of water quality.

In a first aspect the present invention provides a method of isolating virus from a liquid. The method includes the steps of providing a liquid to be processed for virus isolation, suspending anionic resin beads within the liquid, and separating the resin beads from the liquid. It is found that the anionic beads complex with the negatively charged virus during suspension. When the beads are separated from the liquid the virus is thereby isolated from the liquid due to their formation of complexes with the beads.

By suspending the beads, they have the opportunity to disperse throughout the liquid, bringing the beads in proximity to virus particles, where the two can complex. The action creating suspension can be maintained over a sufficient period of time to allow for the complex formation to occur.

In an advantageous embodiment the method can include step of screening the removed beads for the presence of virus. With regard to the suspending step, where the goal is merely to isolate and detect a representative sample of the virus or other pathogen from the media, suspension can occur over a shorter time period when compared to the goal of removing a significant amount of pathogen from the media, which would require a greater time in suspension. Detection methods useful for detecting virus include electron microscopy, cell-culture, latex agglutination, serotyping, enzyme linked immunosorbent assay (ELISA), lateral flow detection, polymerase chain reaction (PCR), reverse transcriptase polymerase chain reaction (RT-PCR) and real time RT-PCR, and integrated cell culture polymerase chain reaction (ICC-PCR). Where PCR is used in the detection, the PCR can employ primers specific for a virus, including primers specific for the detection of Hepatitis A virus, Hepatitis E virus, Rotaviruses (Rotavirus A-G), Poliovirus, Norovirus (including Norwalk virus, Desert Shield virus, Southampton virus, Bristol virus, Lordsdale virus, Toronto virus, Mexico virus, Hawaii virus and Snow Mountain virus), Coxsackie A viruses, Coxsackie B viruses, Echoviruses (including Type 9, 13, 30), Adenoviruses, and Parvoviruses. Additionally, the anionic resin beads can be screened for virus detection without resorting to an elution to separate the beads from the pathogen prior to the screening step. This is a major advantage over other methods, such as those employing filters, where the pathogen must be released from the complex before screening steps can be performed.

In a second aspect the present invention provides a method of isolating and detecting a pathogen in a liquid. The method includes the steps of providing a liquid to be processed for pathogen isolation, suspending anionic resin beads within the liquid, separating the resin beads from the liquid, and screening the anionic resin beads for the presence of a pathogen. The beads can be suspended in the liquid by a variety of means including stirring, inversion and agitation.

Detection methods useful for detecting a pathogen include electron microscopy, cell-culture, latex agglutination, serotyping, enzyme linked immunosorbent assay (ELISA), lateral flow detection, polymerase chain reaction (PCR), reverse transcriptase polymerase chain reaction (RT-PCR) and real time RT-PCR, and integrated cell culture polymerase chain reaction (ICC-PCR). Where PCR is used in the detection, the PCR can employ primers specific for a virus, including primers specific for the detection of Hepatitis A virus, Hepatitis E virus, Rotaviruses (Rotavirus A-G), Poliovirus, Norovirus (including Norwalk virus, Desert Shield virus, Southampton virus, Bristol virus, Lordsdale virus, Toronto virus, Mexico virus, Hawaii virus and Snow Mountain virus), Coxsackie A viruses, Coxsackie B viruses, Echoviruses (including Type 9, 13, 30), Adenoviruses, Parvoviruses, FRNA bacteriophages, somatic coliphages and *Bacteroides fragilis* phages. It is envisioned that the primers can be specific for a particular virus, such as Hepatitis A virus or Adenovirus 41, or primers can be selected that detect related viruses, such as primers that pick up members of the Leviviridae and/or Alloleviviridae or primers that detect a plurality of Rotaviruses. One of skill in the art is capable of designing primers to accomplish such selectivity by focusing on similarities and differences between particular sequences and the desired targets sought to be detected. Additionally, the anionic resin beads can be screened for virus detection without resorting to an elution to separate the beads from the pathogen prior to the screening step.

In certain embodiments the pathogen to be detected can be a virus from a family selected from the group consisting of Adenoviridae, Caliciviridae, Picornaviridae, Hepadnaviridae, Flaviviridae, Reoviridae, Podoviridae, Siphoviridae, Myoviridae, Leviviridae, Inoviridae and Microviridae.

The anionic resin beads can employ functional groups including quaternary amines, tertiary amines, and secondary amines. In an advantageous embodiment the anionic resin bead is a polystyrene spherical bead with a quaternary amine functional group.

In further advantageous embodiments the liquid can be water, milk, juice or homogenized foods. The homogenized food can be produced from a solid food that has been homogenized in a buffer solution to create a liquid sample.

In a third aspect the present invention provides a method of isolating and detecting a virus from a liquid. The method includes the steps of providing a liquid to be processed for virus isolation, suspending anionic resin beads within the liquid, removing the anionic resin beads particles from the liquid, and screening the anionic resin beads for the presence of a virus using a PCR-based technique. The screening step is performed without subjecting the anionic resin beads to elution to separate the beads from the pathogen prior to the screening step. In an advantageous embodiment the anionic resin bead is a polystyrene spherical bead with a quaternary amine functional group. In further advantageous embodiments the anionic resin beads are screened to identify the presence of a bacteriophage.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

The present invention provides a system and associated methods for the capture of viruses and other microorganisms from large volumes of water using ion exchange resins. The principle of ion exchange is based on the fact that these resins are charged with either chloride ($Cl^-$) or hydroxyl ($OH^-$) ions, which are released into water in exchange for less desirable contaminant anions. Anion exchange has traditionally been used in water purification methodologies, as a way to decrease the amount of nitrates, sulphates and other negatively charged ions in the water. It is shown in the present disclosure that these resins can also be effectively employed for the removal of viruses from aqueous/liquid media. While not intending to be bound to any particular theory, one explanation for the results observed herein is that, since anion exchange resins are effective at removing negatively charged ions in water, they are also effective at removing microorganisms, such as viruses, which have a strong net negative surface charge. In this scenario, as water passes through or over the resin, the viruses will be exchanged for, and trade positions with, the loosely held chloride or hydroxyl ions on the resin. This has the effect of concentrating the viruses on the resin. As is shown herein, the resin beads can then be removed and analyzed for the presence of the virus or viruses in question.

Current water concentration methods entail concentration of the target microorganisms onto a filter as sample is passed across the stationary filter, followed by elution. The elution is typically performed in a large volume, often 5 to 15 liters. This dilution by the larger volume then mandates a second re-concentration step before analysis of the concentrated microorganisms can be performed. Due to the number of steps and the complexity, this limits detection of the target microorganisms to laboratory settings.

In contrast to such concentration methods, the present system employs unbound anionic exchange resins to capture target microorganisms. In this schema, a sample is placed into an appropriate container, such as a carboy, and the resin is added to the container. The sample is mixed appropriately (i.e. on a stir-plate, or by some other means of stirring or agitation) such that the beads are suspended within the container, enabling contact with the viruses. Following capture, the resin is removed from the container, and subsequently analyzed for the presence of virus.

Figure 1:
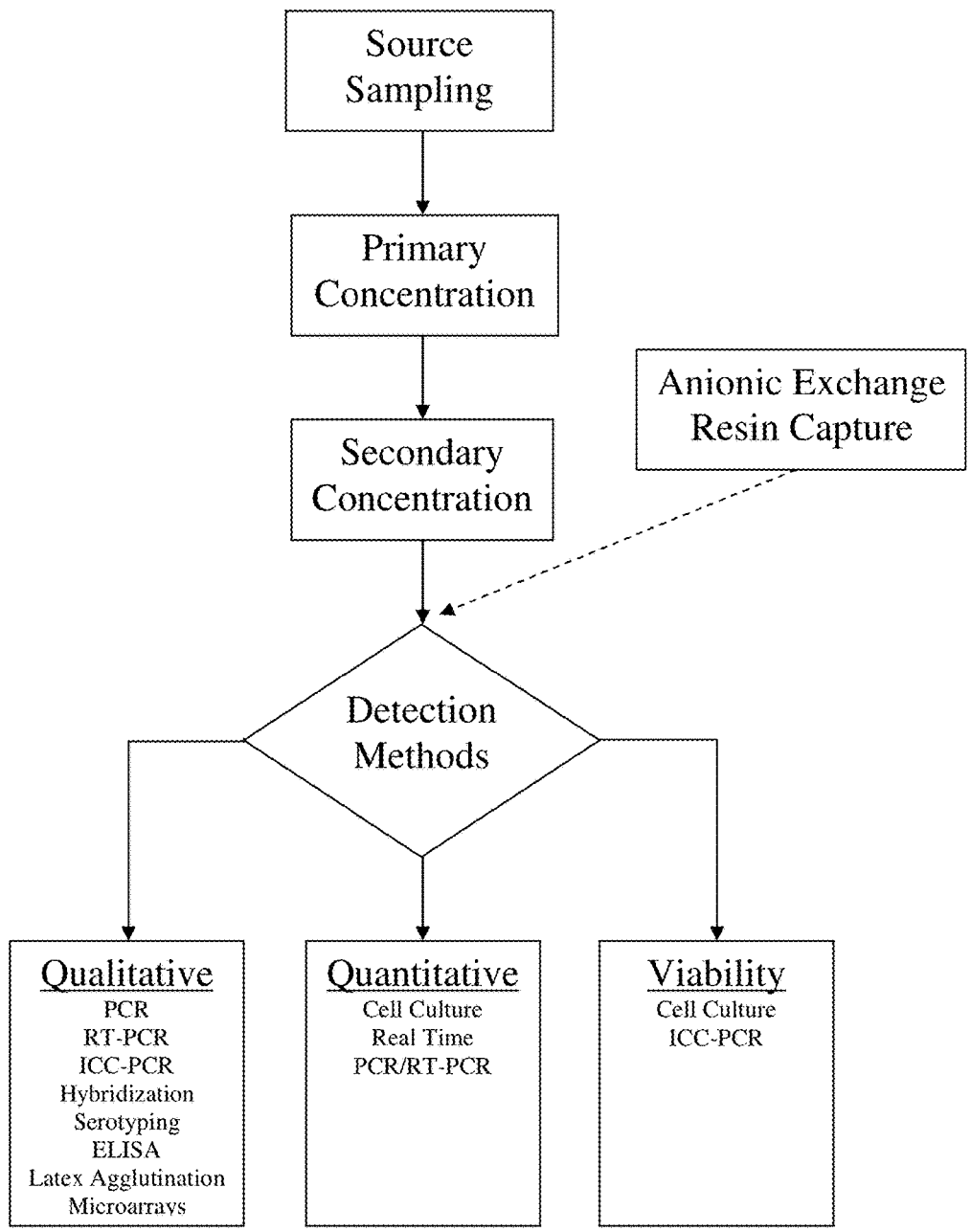
FIG. 1 is a flowchart illustrating the progression of steps involved in traditional water-borne virus detection methodologies. The present invention provides a sampling and concentration schema that eliminates the need for secondary concentration and elution of viruses from filters and membranes, allowing for immediate detection of viruses from the water sample.

Methodologies for the detection of human enteric viruses incorporate several steps, which are summarized in FIG. 1. Generally, viral detection methodology is divided into two phases. The first phase addresses the concentration of viruses from large volumes of water or other aqueous/liquid media. While many water-borne viruses are infective at low doses, effective detection requires their concentration from these levels. Traditional methods of concentration typically entail a primary concentration, where the virus or other contaminant is captured from the water. This may require removal of a smaller sample from the larger volume prior to the primary concentration step if the larger volume is beyond the limits of the system of primary concentration. The capture will typically occur via flow of the sample across a stationary filter, resulting in the virus becoming bound to the filter surface. The bound virus must then be eluted from the filter surface. The elution step, generally necessary to free the bound virus to enable detection, has the undesirable effect of diluting the virus in the elution medium. Such dilution may result in the virus being beyond the limits of detection of the system. Consequently, a secondary concentration step becomes necessary. Once the secondary concentration is complete, detection may begin.

Figure 2:
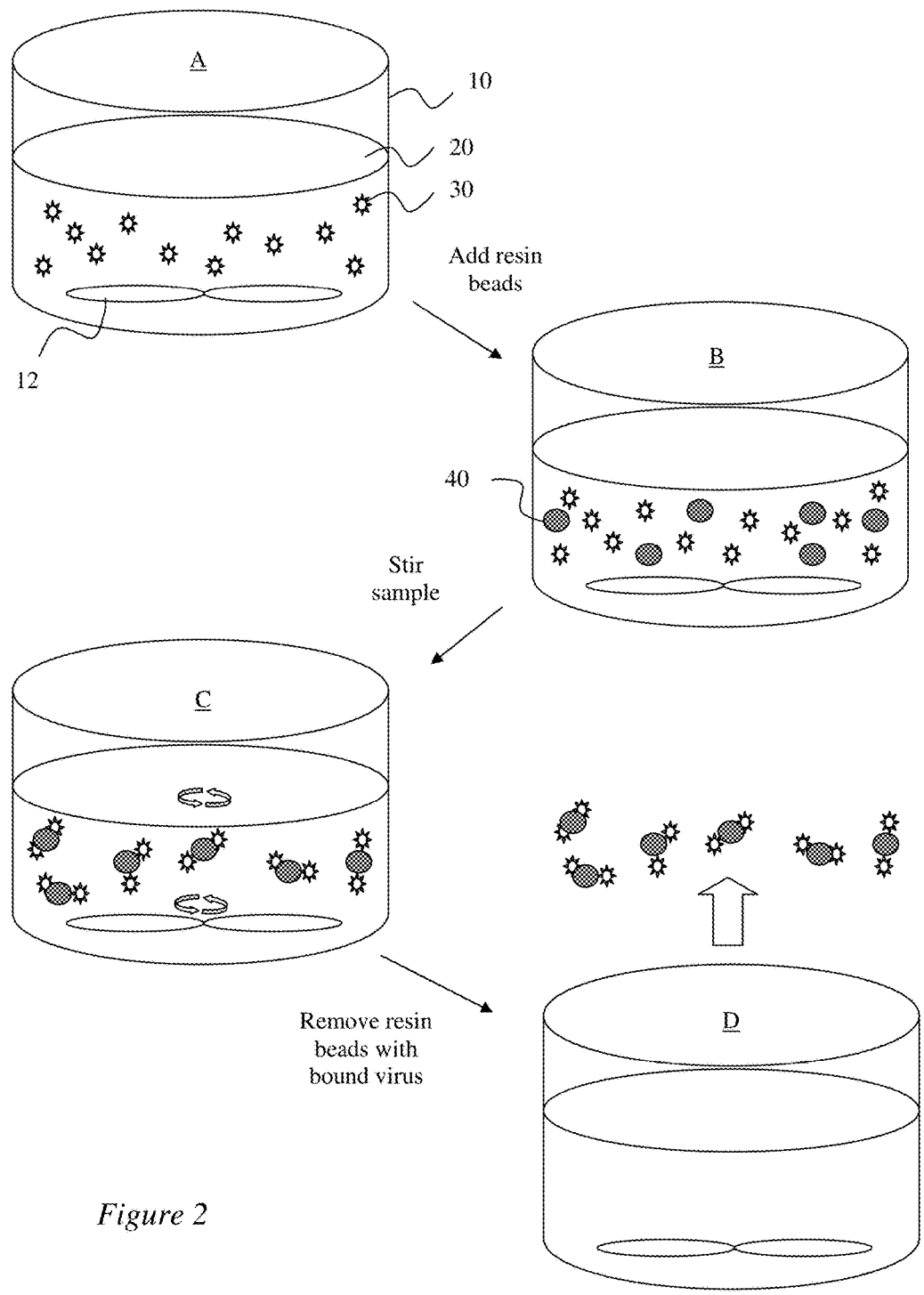
FIG. 2 is an illustration showing the progression of steps in the capture of virus using unbound anionic exchange resin beads.

Turning to FIG. 2 there is shown an exemplary procedure for the isolation of virus particles from a liquid using anionic resins beads. The process begins in step A where there is a container 10 having a stir bar 12 and filled with a liquid 20. The liquid 20 contains a plurality of virus particles 30. In step B, anionic resin beads 40 are added to the liquid 10. In step C, the liquid is stirred by the stir bar 12, resulting in the mixing of the anionic resin beads 40 with the virus particles 30, where the two complex with one-another as they are brought into proximity. In step D the beads 40 are separated from the liquid 10. Because the beads are complexed with virus, separation of the beads results in the isolation of the virus from the liquid. The beads can then be screened directly for the presence of virus without the need for elution of virus from the beads.

In contrast to traditional systems, the present invention eliminates the need for elution and secondary concentration (FIG. 1). It is shown below that capture of virus by unbound anionic charged resins in the water or other aqueous media in the primary concentration may be followed directly by detection, without the need to resort to elution and secondary concentration. Additionally, as discussed below, the present system avoids the costly devices associated with isolation and detection by many of the traditional sampling systems.

The present invention provides a number of other important benefits. Methods for concentration of viruses from large volumes of water or other aqueous sources should be capable of both processing such large volumes and be non-specific and sensitive enough to allow for efficient recovery of all viruses. Therefore, these methods should be based on a non-selective based separation technique, as provided by the disclosed resins, rather than the use of a specific separation method (e.g. immunomagnetic separation). Ideally, these methods should also be developed to allow sample concentration at the source, eliminating the need to transfer large volume water samples to the laboratory. The second phase in the overall detection schema of human enteric viruses from potential water-borne foci addresses the actual detection of virus from the concentrated sample. Usually such detection is accomplished by molecular or cell culture methods. Each of these phases is discussed in more detail below.

Virus Concentration Methods

Traditional virus concentration methods can be divided into primary and secondary steps. The aim of primary concentration is the reduction of water volumes to amounts that can be easily manipulated in the laboratory. Absorption/elution methods [APHA 1998] and ultrafiltration [Jiang, S C, and W. Chu, *J. Appl. Microbiol.* (2004) 97:17-28] are frequently employed to effect concentration of viruses from large volumes of water.

Absorption/elution methods take advantage of the principle that virions are negatively charged at pH 7.0, meaning that the virus particles will adsorb to an electropositive filter. After concentration, an eluant (such as 3% beef extract at alkaline pH ~9.5) is incubated with the filter to elute the viruses. The main advantage of the electropositive filters is that the viruses will absorb to the filter without the need to acidify the sample, unlike electronegative filters which require sample acidification. Electropositive filters have been used in the field to concentrate viruses from a variety of water types including tap water [Lee, S H, and Kim, S J, *Water Res.* (2002) 36:248-256], groundwater [Fout, G S, et al., *Appl. Environ. Microbiol.*, June 2003, 69(6):3158-3164] and river water [Lodder, W J, et al., *Appl. Environ. Microbiol.*, March 2005, 71(3):1453-1461].

Electronegative filters are typically composed of cellulose nitrate or fiberglass resin/glass wool. Large volumes of water (e.g. 1000 liters) can be filtered, and the process can be conducted at the source. To enhance viral absorption to the filter, metal ions such as $Mg^{2+}$ and $Al^{3+}$ are added and the pH of the water sample is acidified (pH 3.5) prior to filtration. Electronegative filters have been employed in the field to concentrate viruses from a variety of samples including finished water, river water and wastewater [In: *Viruses in Water Systems: Detection and Identification.* Block, J. C., Schwartzbrod, L. (1989). VCH, New York]. The reported recovery from seeded samples ranges from 70-94% for enteroviruses [(Block and Schwartzbrod 1989; Lodder, W J, et al., *Appl. Environ. Microbiol.*, March 2005, 71(3):1453-1461].

While charged (electropositive and electronegative) filters are suitable for the analysis of environmental and finished waters, use of these filters may result in lower viral recovery for several reasons including the blockage of the membrane due to high concentrations of organic matter, which also causes competition for binding sites on the filter, and reduced elution efficiency of the viruses [APHA 1998; Myrmel, M E, et al., *Int. J. Food Microbiol*. (1999) 49:85-94]. Also, some charged filters are unsuitable for concentration of particular viruses. For example, rotaviruses can be damaged when the pH of the sample is lowered to pH 3.5 making this type of filter an unsuitable concentration method [Bernasconi et al. 2004].

Ultrafiltration filters employ materials with small pore sizes, allowing for viruses to be retained from the volume of circulating sample. During the ultrafiltration process, the aqueous medium is re-circulated, and subsequently removed, resulting in the concentration of the viruses in the retentate. This process is repeated until the required sample volume and/or viral concentration factor is reached. The filters are usually pre-treated with an eluant to reduce viral absorption onto the membranes. After the required volume is reached a final elution buffer is pumped through the system with the retentate to release any viral particles that have absorbed onto the filter membrane [In: Juliano, J., and M. D. Sobsey. 1997. Simultaneous concentration of *Cryptosporidium*, bacteria, and viruses from water by hollow fiber ultrafiltration. Water Quality Technology Conference. American Water Works Association, Denver, Colo.; Jiang et al. 2001]. The advantages of ultrafiltration include the fact that no pre-treatment of the sample is necessary at acidic pH values and viral concentration does not rely on any binding properties of the virus or the filter. Also, ultrafiltration leads to the concentration of all particles including viruses that are present in the water sample, thereby minimizing bias in concentration of different virus types within the same sample. Several disadvantages of ultrafiltration include the fact that pores can be blocked by organic matter present in environmental water samples, the method can be slow, and ultrafiltration is a fairly expensive process.

After primary concentration, the sample volume may still be too large for use in many detection methods. Therefore, a secondary concentration step is often needed. Methods that result in very high recovery of viruses are desirable, but other factors such as time to concentrate, ease of use, and cost effectiveness must also be considered. Several standard methods are usually employed for secondary concentration of viruses including organic flocculation [Green, D H and Lewis, G D, *Water Res*. (1999) 33:1195-1200], filtration onto charged membranes [APHA 1998], and PEG hydroextraction [APHA 1998]. There are several disadvantages to these secondary concentration methods including the need for equipment such as centrifuges to recover the viruses, and the fact that the recovery of the viruses may also lead to the concentration of compounds that may inhibit downstream detection of the viruses. Finally, depending on the methodology used, viral recoveries are variable.

There have been numerous methods published for the extraction and detection of human enteric viruses from water [Girones, R, et al., *Wat. Sci. Technol*. (1993) 27, 235-241; Enriquez, C E, and Gerba, C P, *Water Res*. (1995) 29, 2554-2560; Juliano and Sobsey 1997; Atmar R L and Estes, M K, *Clin. Microbiol. Rev*., (2001) 14(1):15-37]. These detection methods have been designed to deliver different types of information regarding the microbiological quality of the water. With respect to viruses, current detection methods deliver such information as determining the unambiguous presence/absence of virus, determining viral viability, enumeration of the viral load, and identification of the types of viruses present in the sample.

Virus Detection Methods

Common virus detection methods include electron microscopy, cell-culture, latex agglutination, serotyping, enzyme linked immunosorbent assay (ELISA) and molecular methods (polymerase chain reaction (PCR), reverse transcriptase polymerase chain reaction (RT-PCR) and real time RT-PCR) (FIG. 1). In some instances several of these techniques are employed simultaneously to increase the sensitivity of the assay.

The presence/absence and viability of viruses can be demonstrated using cell culture methods, where the cytopathic effects (CPE) of the virus on a given cell line can be observed. Currently, cell culture is the only method that is capable of demonstrating the viability of viruses. The minimum number of virions required for detection by cell culture is approximately 1-10 per gram of sample [Koopmans M, and Duizer E., *Int J Food Microbiol*. (2004) 90(1):23-41], making this method suitable for environmental samples. Viral load can be enumerated using cell culture-based plaque assays. Cell culture can be used to detect the presence of non-target viruses as well as target viruses [(Lee, H K, et al., Applied and Environmental Microbiology, (2004) 70(6): 3632-3636]. For example, Lee, H K et al. reported that cell culture assays showed higher concentrations of viral particles than despite the increased sensitivity of the ICC-PCR assay. After investigation, it was found that some of the CPE in the cell culture assays were caused by reovirus, rather than the suspected enteroviruses or adenoviruses that were the targets of the analysis. Plaque assays have been described for adenoviruses, enteroviruses, rotaviruses and astroviruses [Koopmans M, and Duizer E., *Int J Food Microbiol*. (2004) 90(1):23-41].

Some of the problems associated with cell culture include its expense, to conduct cell culture can require up to 14 days for results, and the availability of appropriate cell lines (appropriate cell lines are not available for all enteric viruses; e.g. Noroviruses), CPE are not observed for some viruses (e.g. adenoviruses, especially type 40 and 41 [Lee, S H and S J Kim, *Water Res*. (2002) 36, 248-256] and Hepatitis [Jiang, S C, and W. Chu, *J. Appl. Microbiol*. (2004) 97:17-28]), or the virus may be unculturable. In addition, some cell lines are selective of virus types (e.g. BGMK cells seem to select for enteroviruses [Lee, S H and S J Kim, *Water Res*. (2002) 36, 248-256]) at the expense of other viruses present in the sample. To overcome these issues, other detection methods are often employed in conjunction with cell culture and more than one cell-line is often employed to ensure that the assay detects the maximum number of viral strains present [APHA 1998; Lee, S H and S J Kim, *Water Res*. (2002) 36, 248-256].

Molecular methods have become the preferred way to investigate viral presence in water samples [Bernasconi et al. 2004]. Molecular methods can detect the presence/absence of enteric viruses, are rapid, sensitive, specific and can detect viruses that cannot be detected by cell culture. All of the molecular methods (e.g. polymerase chain reaction (PCR), nested/semi-nested polymerase chain reaction (n-PCR, sPCR), and reverse transcriptase PCR (RT-PCR)) give presence/absence data (qualitative), but there is no indication of the viral load or infectivity. Real Time RT-PCR and real time PCR can be employed when there is a need to quantify the viral load. In theory, as little as a single virion can be detected using molecular-based methods, making these methods more sensitive than any other detection method [Koopmans M, and Duizer E., *Int J Food Microbiol*. (2004) 90(1):23-41].

Industrial Application

The anion resin-based virus capture method is capable of concentrating viruses from large volumes of liquefied sample, including water, juice, milk, and homogenized food (i.e. solid food that has been pulsified in a liquid medium). Therefore, it is expected that the resin based method of concentration will find application in recreational and drinking water sampling as part of public health agency testing methodology, and water sampling as part of bio-defense testing.

The method is also expected to find use in the food industry where water, juices, and milk can be tested for the presence of enteric viruses. In addition, it is expected that solid food (such as seafood or produce) can also be sampled, after it is first homogenized in an appropriate buffer.

All of the current water concentration methods entail concentration of the target viruses on a filter, followed by elution (usually in a large volume [5 to 15 liters]), and a second reconcentration step (by ultrafiltration or reverse osmosis) before analysis of the concentrated microorganisms can occur. In contrast, the adsorption of the viruses onto suspended anionic exchange resin beads enables the direct analysis of the presence of the target viruses (by PCR or cultural techniques), without the need for elution. In addition, the entire water sample (up to 60 liters) can be saved for future (and more in depth analysis).

Pathogen/Viruses: The anionic resin particles complex with pathogens exhibiting a net negative charged surface area including eukaryotic virus families and genera, such as Adenoviridae, Caliciviridae, Picornaviridae (Enteroviruses, Coxsackieviruses and Echoviruses), Hepadnaviridae, Flaviviridae, Reoviridae, Parvoviridae, and Astroviridae, and bacteriophage family and genera, such as Myoviridae, Podoviridae, Siphoviridae, Leviviridae, Inoviridae and Microviridae. Some of the more common viral pathogens associated with waterborne illnesses and amenable to ioslation and detection with the methodologies taught herein include Hepatitis A virus, Hepatitis E virus, Rotaviruses (Rotavirus A-G), Poliovirus, Norovirus (including Norwalk virus, Desert Shield virus, Southampton virus, Bristol virus, Lordsdale virus, Toronto virus, Mexico virus, Hawaii virus and Snow Mountain virus), Coxsackie A viruses, Coxsackie B viruses, Echoviruses (including Type 9, 13, 30), Adenoviruses, Parvoviruses.

Definitions

As used throughout the entire application, the terms "a" and "an" are used in the sense that they mean "at least one", "at least a first", "one or more" or "a plurality" of the referenced components or steps, unless the context clearly dictates otherwise. For example, the term "a cell" includes a plurality of cells, including mixtures thereof.

The term "and/or" whereever used herein includes the meaning of "and", "or" and "all or any other combination of the elements connected by said term".

The term "about" or "approximately" as used herein means within 20%, preferably within 10%, and more preferably within 5% of a given value or range.

Other than in the operating examples, or unless otherwise expressly specified, all of the numerical ranges, amounts, values and percentages such as those for amounts of materials, times and temperatures of reaction, ratios of amounts, values for molecular weight (whether number average molecular weight ("$M_n$") or weight average molecular weight ("$M_w$"), and others in the following portion of the specification may be read as if prefaced by the word "about" even though the term "about" may not expressly appear with the value, amount or range. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used.

As used herein, the term "comprising" is intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

As used herein, the term "virus" refers to any of a large group of submicroscopic infective agents that contain a protein coat surrounding an RNA or DNA core of genetic material but no semipermeable membrane, that are capable of growth and multiplication only in living cells, and that cause various important diseases in humans, animals, or plants. Furthermore, as used herein, the term virus includes the bacteriophages. The term "bacteriophage" refers to a virus that infects bacteria. Thus, within the greater group of viruses there exist the eukaryotic viruses (e.g. animal viruses such as Hepatitis A virus) and the prokaryotic viruses (i.e. bacteriophages).

As used herein, the term "pathogen" refers to any type of biological entity that infects a host organism, wherein the infection may result in disease of the host. The term includes the bacteriophages, a group of viruses that infect bacteria.

Anion exchange resin particles can be used as adsorbent particles. These resins are characterized by a functional group exhibiting a net positive charge. Examples of anion exchange resin that can be used to adsorb a virus include strong and medium strong, as well as weak basic anion exchange resins. The terms strong, medium strong and weak basic anion exchange resins are typically used to describe the particles. Strong basic anion exchange resin typically contain quaternary ammonium groups, medium strong resins usually have tertiary amine groups and weak basic resins usually have secondary amines as the anion exchange functions. Examples of anion exchange resins that are commercially available for use in this invention include AMBERLITE® IRA-900, which is a strong base (quaternary ammonium chloride) 0.53 mm, capacity 1.0 meq/ml (wet); AMBERLITE® IRA-458: strong base (quaternary ammonium chloride), 0.50 mm, capacity 1.25 meq/ml (wet); AMBERLITE® IRA-93: weak base (free base), 0.49 mm, capacity 1.2 meq/ml (wet); AMBERLITE® IRA-958: strong base (quaternary ammonium chloride), 0.49 mm, capacity 0.8 meq/ml (wet). Resins such as AMBERLITE® IRA-900 are used for deionization of water and removal of organics. Advantageously, the resin employed will be a strongly basic anionic resin, such as a resin employing quaternary amines, although the spectrum of weaker anionic resins strengths can be utilized where applicable.

As used herein, "elution" refers to the process of using a solvent to extract an adsorbed substance from a solid adsorbing medium.

Unless defined otherwise, all technical and scientific terms used herein have the same meaning as commonly understood by one of ordinary skill in the art (e.g., in cell culture, molecular genetics, nucleic acid chemistry, hybridisation techniques and biochemistry). Standard techniques are used for molecular, genetic and biochemical methods. See, generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) 4th Ed, John Wiley & Sons, Inc.; as well as Guthrie et al., Guide to Yeast Genetics and Molecular Biology, Methods in Enzymology, Vol. 194, Academic Press, Inc., (1991), PCR Protocols: A Guide to Methods and Applications (Innis, et al. 1990. Academic Press, San Diego, Calif.), McPherson et al., PCR Volume 1, Oxford University Press, (1991), Culture of Animal Cells: A Manual of Basic Technique, 2nd Ed. (R. I. Freshney. 1987. Liss, Inc. New York, N.Y.), and Gene Transfer and Expression Protocols, pp. 109-128, ed. E. J. Murray, The Humana Press Inc., Clifton, N.J.).

The following examples are provided for the purpose of illustration and are not intended to limit the scope of the present invention.

Example 1—Ion Exchange Resins to Capture Microorganisms from Large Volumes of Tap Water To assess the ability of anion exchange resins to efficiently capture viruses from water, several surrogates of enteric viruses, the F-specific RNA (FRNA) phages, were inoculated into water, followed by an assessment of the ability of an anionic exchange resin to concentrate the phages from the water. Many reports have described the use of FRNA phages (especially MS2) as acceptable surrogates for such enteric viruses as the noroviruses and Hepatitis A virus, due to the similarity in type of nucleic acid, and the morphological and structural similarities between both groups of viruses [Bae, J and Schwab, K J, Appl Environ Microbiol. (2008) 74(2): 477-84]. In addition to acting as surrogates of enteric viruses in laboratory settings, bacteriophages can serve as surrogates for the presence of contamination outside of the lab. For example, high levels of FRNA bacteriophage contamination have been shown to be strongly associated with harvest area fecal pollution and with shellfish associated disease outbreak [Dore, W J, et al., Appl Environ Microbiol. (2000) 66(4):1280-1285; Leclerc, H., et al., J Appl Microbiol (2000) 88: 5-21]. Importantly, FRNA bacteriophage contamination was shown to be consistent with incidence of enteric virus disease, such as disease caused by Norwalk-like virus.

Coliform monitoring has historically been used as the primary indicator of contamination and fecal pollution in water supplies [Leclerc, H., et al., J Appl Microbiol (2000) 88: 5-21]. The impetus for this approach was founded in the difficulty of attempting to individually detect the multiplicity of pathogens that might be present in a source, coupled with the ease, timeliness, specificity and cost-effectiveness of the detection of E. coli or total coliforms in a water sample. Despite these benefits, certain advantages accrue from the use of bacteriophages rather than bacterium as surrogate indicators of environmental contaminants, especially with respect to environmental contamination by enteric viruses. Some of the benefits include the fact that bacteriophages are better mimics of the diffusion characteristics of viruses. Because bacteriophages are viruses, and have sizes more closely resembling those of enteric viruses than do the larger bacteria, they have transit times analogous to that of the enteric viruses. Enteric viral pathogens are also generally more resistant to environmental conditions, and sewage or water treatment processes, than the coliforms used as indicators of their presence. Bacteriophages, on the other hand, exhibit similar resistance to environmental conditions, and sewage or water treatment processes, to the enteric viruses. Lastly, molecular detection of bacteriophages can prove less costly and time consuming for routine monitoring than detection of many enteric viruses.

Figure 3:
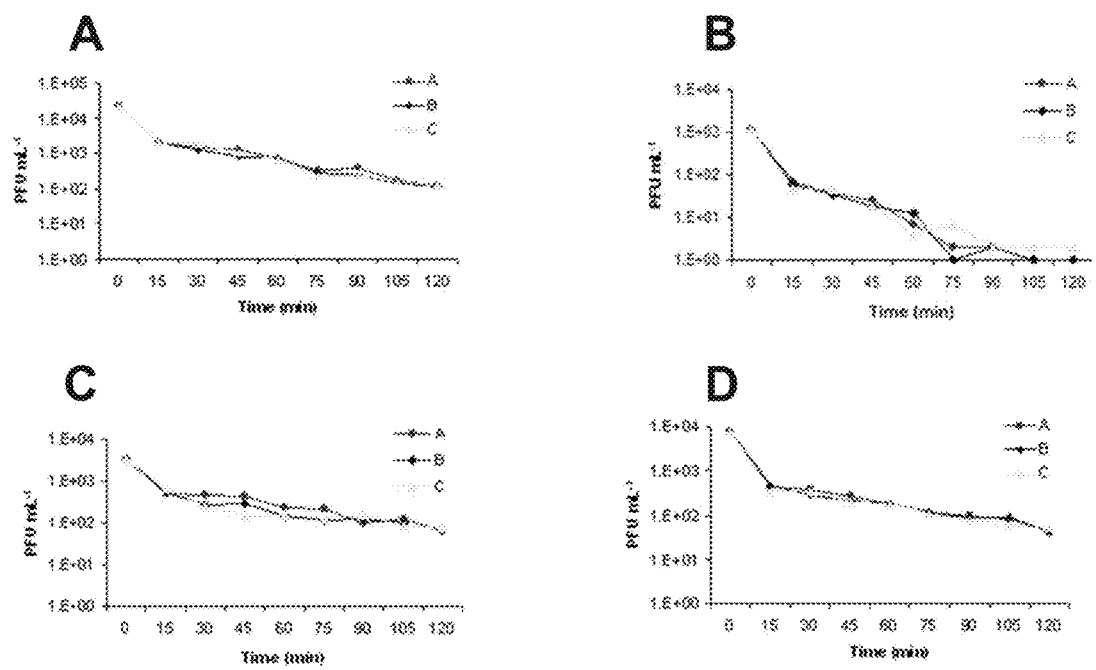
FIG. 3 is a set of graphs illustrating the anionic exchange resin capture efficiencies for the FRNA phages MS2 (A), Qβ (B), SP (C), and GA (D). The graphs show the amount of phages left in the water at each sample point. A decrease in the concentration of phages in the water indicates that the phages have been removed from the water (i.e. they have been bound to the resin beads). Each experiment was replicated three times, and this is shown on each graph as separate lines (A, B, or C). Note that the C replicate appears faintly and is largely coextensive with the B replicate at most points measured.

Thus, to assess the ability of anion exchange resins to efficiently capture viruses from water, FRNA phages MS2, GA, SP and Qβ were individually seeded into 50 mL volumes of tap water at a concentration of $10^4$ PFU mL$^{-1}$. One gram of anionic exchange resin (Amberlite® IRA 900) was added to each water sample. The samples were continually agitated and aliquots were withdrawn at 15 minute intervals for 2 hours, and assayed for phage via the double layer plaque assay. The results are shown in FIG. 3. Capture efficiency utilizing the anionic exchange resin was found to be greater than 82%, 94%, and 98% for all phages after 15, 60 and 120 minutes, respectively (Table 1).

TABLE 1

|  | MS2 | GA | Qβ | SP |
| --- | --- | --- | --- | --- |
| 15 minutes | 90.8% | 94.7% | 95.1% | 82.9% |
| 30 minutes | 93.1% | 95.7% | 96.8% | 90.2% |
| 45 minutes | 95.3% | 97.1% | 98.3% | 91.5% |
| 60 minutes | 96.7% | 97.8% | 99.3% | 94.6% |
| 75 minutes | 98.7% | 98.6% | 99.7% | 95.6% |
| 90 minutes | 98.5% | 98.8% | 99.8% | 96.2% |
| 105 minutes | 99.3% | 99.0% | 99.9% | 96.9% |
| 120 minutes | 99.4% | 99.4% | 99.9% | 98.0% |

Table 1 presents the anionic resin capture efficiencies for the four FRNA phages tested. The percentages indicate the concentration of phages bound onto the resin beads, calculated by dividing the concentration of each phage in the water sample at the different time periods by the concentration of each phage initially seeded in water (approximately $10^4$ PFU/ml), multiplying by 100 (to give the percentage of phages still in the water), and subtracting that value from 100.

Example 2—Ion Exchange Resins to Capture Microorganisms from Large Volumes of Reservoir Water The results from the tap water experiments showed that the anionic exchange resin was extremely effective at capturing the FRNA phages in tap water. Accordingly, experiments were conducted to determine whether the resin could capture phages from other types of water, and also from larger volumes. Therefore, water was obtained from a California reservoir, and the water was divided into two 400 mL aliquots. Each aliquot was placed into a separate sterile 500 mL Duran bottle. One bottle served as the control while the other bottle served as the test sample. Both bottles were seeded with the FRNA phage MS2 at a final concentration of $10^5$ PFU/ml. One gram of the anion exchange resin was added to the test sample. Both bottles were placed on stir plates with magnetic stir bars, and stirred continuously at room temperature for two hours. At 30 minute intervals, beads were allowed to settle in the test bottle, and 1 ml aliquots of water were removed from each sample. The aliquots were serially (10-fold) diluted in phage buffer, and 100 µL of each dilution was plated using the top-agar overlay method, and incubated at 37° C. The results are shown in FIG. 4.

Figure 4:
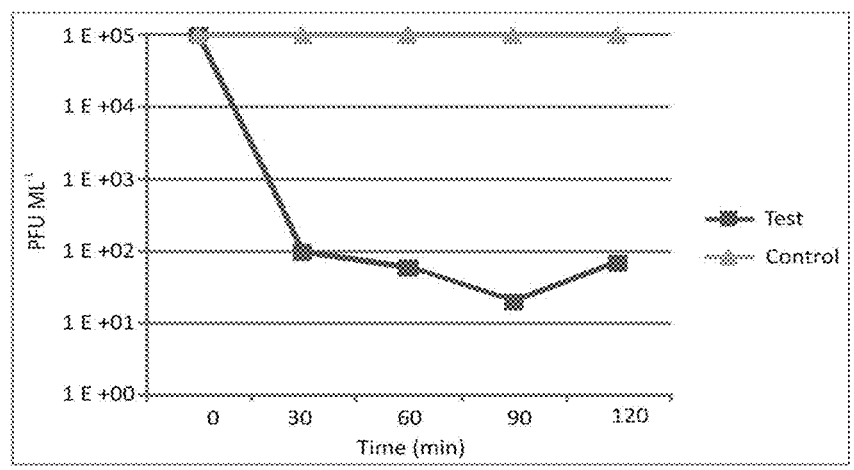
FIG. 4 is a graph illustrating the anionic exchange capture efficiencies for the FRNA phage MS2 seeded at a starting concentration of $10^5$ PFU/ml into reservoir water. A decrease in the concentration of phage MS2 in the water (relative to the control) indicates that the phage has been removed from the water by capture on the beads.

As shown in FIG. 4, the resin performed even better in the reservoir water than in the tap water. The resin captured 99.9% of the MS2 in the reservoir water within the first 30 minutes, as compared to 93.1% of the MS2 in the tap water within the same time period. At 60 minutes, 99.94% of the MS2 had been captured from the reservoir water as compared to 96.7% from the tap water. At 90 minutes, 99.98% had been captured from the reservoir water as compared to 98.5% from the tap water. Finally, at 120 minutes, 99.93% had been captured from the reservoir water as compared to 99.4% in the tap water.

These results are noteworthy for three reasons. First, the results indicate that the resin is extremely effective at capturing surrogate viruses in different types of water. Also, the results show that the method is scalable, which is further demonstrated by the ability to capture surrogate viruses from volumes as large as 20 liters using the VacBAC device (see Example 6, below). Finally, it was also found that the phages remained infectious when bound to the resin. This was shown by enriching the phages in the presence of their bacterial host ($E.$ $coli_{Famp}$), followed by detection (data not shown) with a lateral flow device as described below.

Example 3—Phage RNA Detection from Resin Beads

Figure 5:
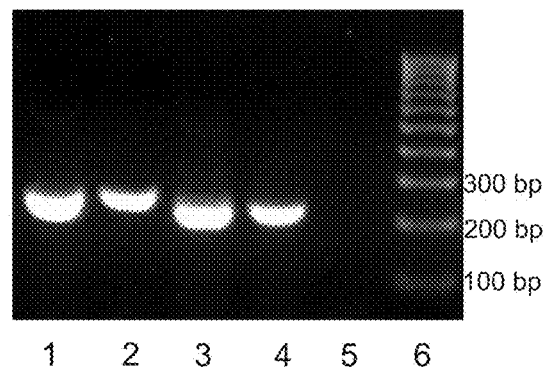
FIG. 5 is an image illustrating the agarose gel electrophoresis of RT-PCR amplicons of the four FRNA phages representing each of the four FRNA serogroups. Lane 1, MS2 (expected band size 266 bp); Lane 2, GA (expected band size 266 bp); Lane 3, QB (expected band size 225 bp); Lane 4, SP (expected band size 225 bp); Lane 5, negative control; Lane 6, 100 bp ladder.

To show that the phages were bound to the beads, as opposed to, for example, simply becoming inactivated in the water because of the beads, a reverse-transcriptase polymerase chain reaction (RT-PCR) assay was used to detect FRNA nucleic acid directly off of beads. Anionic exchange resin beads were directly suspended in nucleic acid (RNA) isolation buffer, and then subjected to a one step RT-PCR assay using a multiplex primer set. The primer set is specific for the two genera of the FRNA phages; the Leviviridae and Alloleviviridae. The results show that phage RNA bound to the resin beads was capable of detection by RT-PCR (FIG. 5). One noteworthy aspect of this result is that it shows that the phages do not need to be eluted off of the beads before detection. This is a major advantage of this concentration method, as compared to other, filtration-based concentration methods because those other methods require that the phages are eluted from the filter and re-concentrated (i.e. a secondary concentration) prior to analysis.

Example 4—Sensitivity of Anionic Exchange Resin Capture

Figure 6:
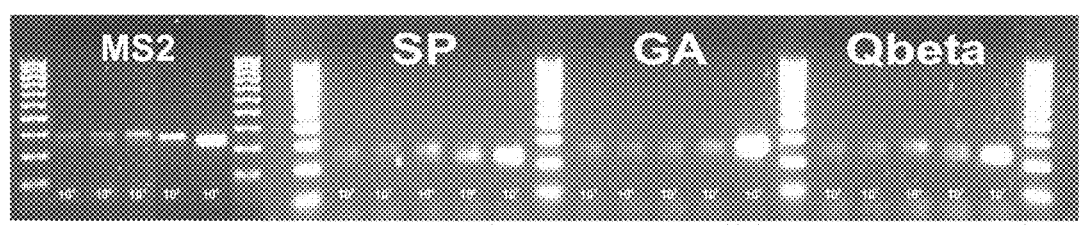
FIG. 6 is an image illustrating the sensitivity of anionic exchange resin capture. The RT-PCR assay detected as few as $10^0$ PFU/ml of phage indicating that the resin was able to capture very low levels of phage in the water. The figure shows gel electrophoresis results of the RT-PCR assay for all phages tested. For a given phage, lanes 1 and 7 contain a 100 bp ladder, and lanes 2-6 contain the RT-PCR results obtained from different starting concentrations ($10^0$ to $10^8$ PFU/ml) of the phages seeded into the water.

The sensitivity of the anionic resin bead concentration process was analyzed. To conduct this experiment, 50 ml water samples were seeded with several different phage concentrations ($10^0$, $10^2$, $10^4$, $10^6$, and $10^8$ PFU/ml), 1 gram of the resin was added to the seeded water and the resin was used to capture the phages as described above. One difference from the prior experiments was that, in this experiment, a sample was removed at 60 minutes instead of at 15 minute intervals over the course of 120 minutes. The rationale for performing capture for 60 minutes was that, as observed in the previous capture experiments, greater than 94% of all phages were captured at 60 minutes. Thus, the selected time represented a good compromise between capture time and capture efficiency. To determine the sensitivity of the capture method, the same RT-PCR assay described above was utilized. The results (FIG. 6) show that the RT-PCR method was able to detect as few as $10^0$ PFU/ml for all phages. Therefore, the beads are very efficient at capturing even low concentrations of phages from water.

Example 5—Lateral Flow-Based Detection of FRNA Phages Following Enrichment

Figure 7:
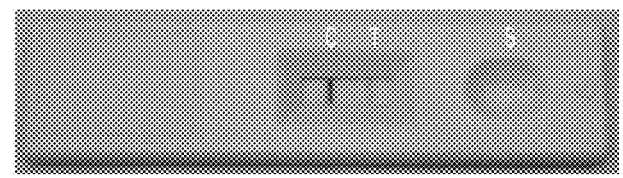
FIG. 7 is an image illustrating lateral flow-based detection of FRNA phages following enrichment.

Viability of the phages (i.e. infectious capacity) after being bound to the resin beads was determined. To test for infectivity, an enrichment step was developed to increase the number of FRNA phages. Briefly, following capture with the resin, the resin, with bacteriophages attached, was isolated from the water sample, and directly suspended into a broth culture containing the bacterial host, $E.$ $coli$. The enrichment allowed the bacteriophages to infect the $E.$ $coli$ and replicate, thereby increasing their numbers, to a high enough concentration to be detectable by the lateral flow device. Following enrichment, phage was detected by detected by lateral flow device (FIG. 7). These results show that the resin capture step could be used in conjunction with a cell culture assay to determine the presence of viable viruses.

Example 6—Scale-Up to Larger Volumes for Detection

Based on the experiments and results described above, a two stage process was developed, which entails sampling large volumes of water (up to 60 liters) and concentrating the FRNA phages in the first stage, or phase, followed by a second stage employing a detection method (RT-PCR) to identify the presence of any FRNA phages.

Figure 8:
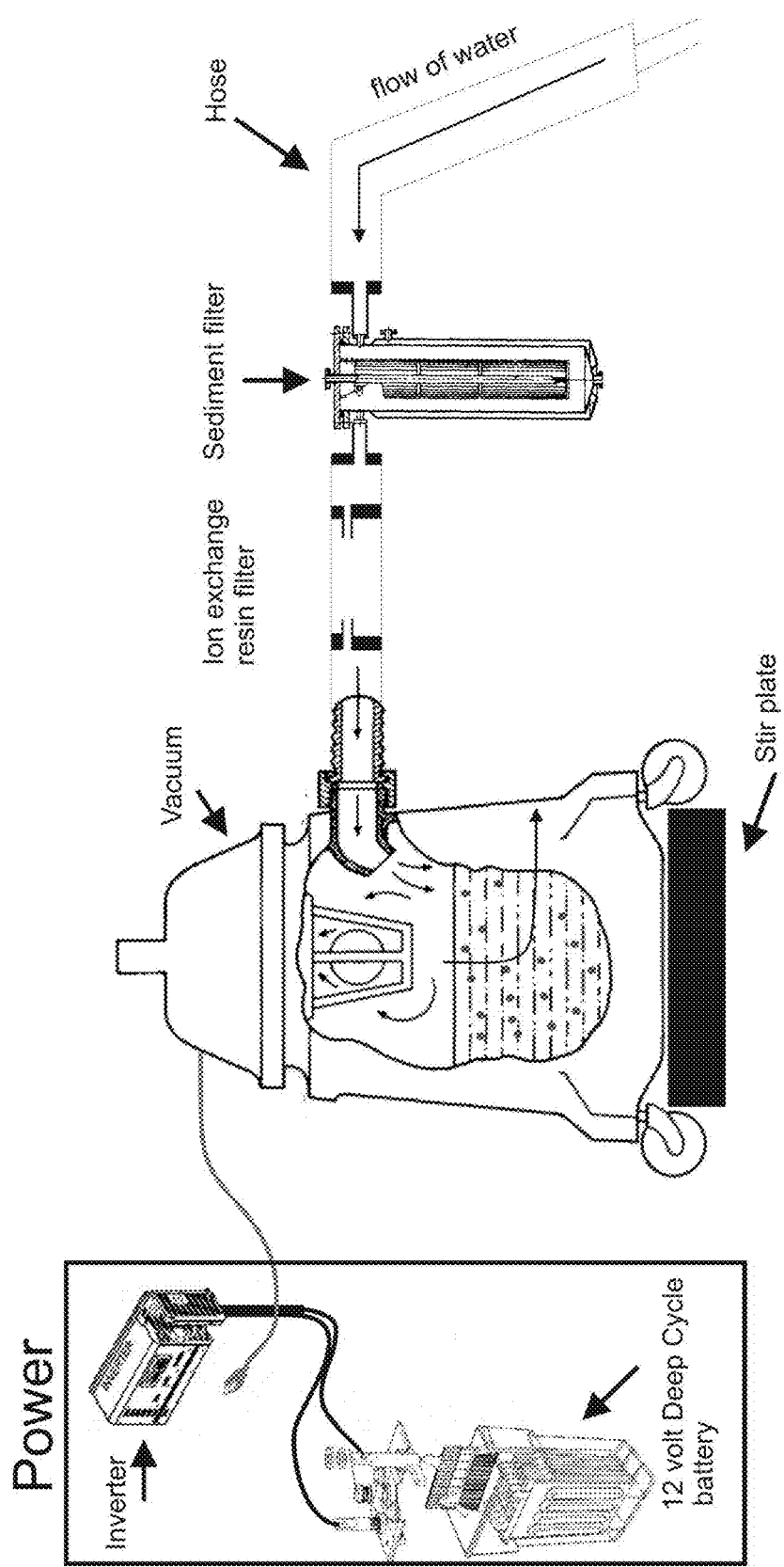
FIG. 8 is a schematic of the Vacuum Based Adsorption of Contaminants (VacBAC) device. The VacBAC is a modified wet vacuum that contains a sediment removal filter in the hose. Water is sampled (sucked up) via the hose, and any particulates or sediment is removed via the sediment filter. The water is sucked into the vacuum container. After sampling is complete, the resin beads are added to the container and the water sample is agitated, allowing the viruses or other pathogens to attach to the resin beads. Following capture, the resin beads are collected for downstream detection of the viruses or other pathogens. The VacBAC is powered by a 12 volt deep cycle battery, which is attached to a 110 volt AC inverter.

The first phase of the process was facilitated by the development of the large scale sampling and concentration device called the Vacuum Based Adsorption of Contaminants (VacBAC) device (FIG. 8). In its current configuration the VacBAC is capable of sampling 60 liters. However, the technology is scalable, making the sampling of larger volumes of water, in excess of 100 liters, feasible.

The VacBAC device is a sampling device in which the liquid sample is introduced to the canister of the VacBAC via a vacuum. Once the sample enters the canister, it interacts with the previously described resin beads, which are constantly agitated to remain in suspension. The beads capture the microorganisms as described, and following capture, the liquid sample is removed from the sample canister. The remaining resin beads can then be collected and analyzed for the presence of the target microorganism. The VacBAC is capable of concentrating viruses and bacteria from large volumes of liquefied sample, including water, juice, milk, and homogenized food (i.e. solid food that has been pulsified in a liquid medium). Therefore, the VacBAC will find application in recreational water sampling as part of public health agency testing methodology, and water sampling as part of bio-defense testing. The VacBAC is also expected to find use in the food industry where water, juices, and milk can be tested for the presence of foodborne pathogens. In addition, it is expected that solid food can also be sampled by the VacBAC, after it is first homogenized in an appropriate buffer.

Figure 9:
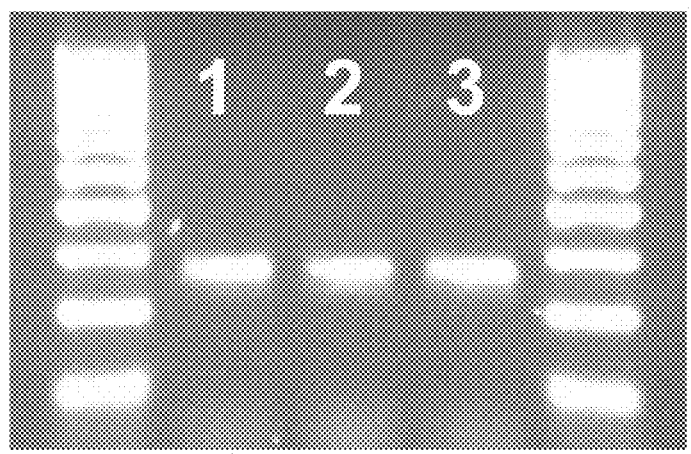
FIG. 9 is an image showing an evaluation of the VacBAC in combination with RT-PCR for the rapid detection of FRNA phage MS2. Lanes 1 and 5, 100 bp ladder. The lanes indicated by the numbers 1, 2 and 3 indicate the number of times the sample was circulated prior to detection of the RNA phages. Thus, in the lane identified as "1" the sample passed the resin a single time prior to testing by RT-PCR. In lane 2, the samples passed the resin twice prior to testing for phage.

RT-PCR was used in conjunction with the sampling and concentration capability of the VacBAC to detect FRNA phages in water. For this experiment, 20 liters of tap water was spiked with $10^5$ PFU/ml of phage MS2. To concentrate the FRNA phage with the VacBAC, 1 gram of ion exchange resin was added to the ion exchange filter in the device (FIG. 8), and the 20 liter sample was processed by suction of the water up through the VacBAC hose. The water flowed through the cartridge filter and the second (ion exchange resin-based) filter, and then into the wet vacuum cartridge. The flow rate was approximately 1 liter per minute, so the 20 liter sample was concentrated within 20 minutes. Initial experiments showed that approximately 30% of the MS2 phage was concentrated during the first pass of water sampling. Therefore, the water was re-circulated twice more to evaluate the ability of the VacBAC to isolate more phage from the water sample. Following sampling, the ion exchange resin, with the FRNA phage attached, was removed from the filter, and the entire 1 gram sample was tested by the RT-PCR assay as described above. The results are shown in FIG. 9.

The results show the ability of an anionic resin to capture viruses from large (40 liters) volumes of water, followed by downstream detection. While the capabilities of the resin were demonstrated in conjunction with the VacBAC system, the resin does not need to be used with the VacBAC, but can be used in a stand-alone fashion to capture virus. To effect concentration and detection, a sample is placed into an appropriate container, such as a carboy, and the resin is added to the container. The sample is mixed sufficiently, such as with a stir plate or some means of agitation, to result in the suspension of the beads within the container. The suspension of the beads in the sample facilitates contact with any virus within the sample. Following capture of the virus on a resin bead(s), the resin is removed from the container, and subsequently analyzed for the presence of virus. Resins can be separated from the aqueous media by a variety of methods, including allowing the beads to settle, followed by decanting or by filtration through a filter paper, allowing the water, but not the beads to flow through.

The VacBAC device is based on adsorption of the microorganisms onto anionic exchange resin beads. Following adsorption the beads can be analyzed directly for the presence of the target microorganism (by PCR or cultural techniques), without the need for elution. This allows for analysis of the target organisms directly in the field. In addition, the entire water sample (up to 60 liters) can be saved for future (and more in depth analysis).

The results show that anionic exchange resin beads are an effective means for the concentration of FRNA phages from water. Due to similar physico-chemical properties, the FRNA phages are useful surrogates of human enteric viruses, making these results directly applicable to the development of methods for the concentration and detection of enteric viruses. The results also indicated the effectiveness of using RT-PCR to detect viruses, using FRNA phages as surrogates, bound to the anionic exchange resin beads.

While the results presented herein detail the isolation and detection of bacteriophages, the resins have also been used to concentrate feline calicivirus, which is used as a surrogate for noroviruses, and adenoviruses types 5 and 41. Real time PCR was then effectively used to detect the viruses (data not shown). Feline calicivirus is a RNA virus, and the adenoviruses are DNA viruses. Thus, the technology has proven effective is detecting both types of eukaryotic viruses (i.e. RNA and DNA viruses) in addition to the bacteriophages.

All references cited in the present application are incorporated in their entirety herein by reference to the extent not inconsistent herewith.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method of isolating virus from a liquid comprising the steps of:
    providing a liquid or liquefied homogenized food to be processed for virus isolation;
    suspending anionic resin beads having a diameter of about 0.49 mm or larger within the liquid or liquefied homogenized food;
    sedimenting the beads to the bottom of the liquid or liquefied homogenized food, wherein the beads are sedimented by the force of atmospheric gravity; and
    separating the sedimented beads from the liquid or liquefied homogenized food, whereby the beads complex with the virus during suspension effecting the isolation of the virus from the liquid or liquefied homogenized food upon separation of the beads.

2. The method according to claim 1 further comprising the step of screening the separated beads for the presence of virus.

3. The method according to claim 2 wherein the screening method is selected from the group consisting of electron microscopy, cell-culture, latex agglutination, serotyping, enzyme linked immunosorbent assay (ELBA), polymerase chain reaction (PCR), reverse transcriptase polymerase chain reaction (RT-PCR) and real time RT-PCR, and integrated cell culture polymerase chain reaction (ICC-PCR).

4. The method according to claim 3 wherein the PCR employs primers for a virus selected from the group consisting of Hepatitis A virus, Hepatitis E virus, Rotaviruses (Rotavirus A-G), Poliovirus, Noroviruses, Coxsackie A viruses, Coxsackie B viruses, Echoviruses, Adenoviruses, Parvoviruses, FRNA bacteriophages, somatic coliphages and *Bacteroides fragilis* phages.

5. The method according to claim 2 wherein the anionic resin beads are not subjected to elution to separate the beads from the virus prior to the screening step.

6. The method according to claim 1 where the liquid is selected from the group consisting of environmental water samples, drinking water, milk, and juice.

7. The method according to claim 1 wherein the liquified homogenized food is a solid food that has been homogenized in a buffer solution to create the liquefied homogenized food.

8. A method of isolating and detecting a virus in a liquid comprising the steps of:
    providing a liquid to be processed for virus isolation and detection;
    suspending anionic resin beads having a diameter of about 0.49 mm or larger within the liquid;

sedimenting the anionic resin beads under atmospheric gravity;

separating the anionic resin beads from the liquid; and screening the anionic resin beads for the presence of the virus.

9. The method according to claim 8 wherein the screening method is selected from the group consisting of electron microscopy, cell-culture, latex agglutination, serotyping, enzyme linked immunosorbent assay (ELISA), polymerase chain reaction (PCR), reverse transcriptase polymerase chain reaction (RT-PCR) and real time RT-PCR, and integrated cell culture polymerase chain reaction (ICC-PCR).

10. The method according to claim 9 wherein the PCR employs primers for a virus selected from the group consisting of Hepatitis A virus, Hepatitis E virus, Rotaviruses (Rotavirus A-G), Poliovirus, Noroviruses, Coxsackie A viruses, Coxsackie B viruses, Echoviruses, Adenoviruses, Parvoviruses, FRNA bacteriophages, somatic coliphages and *Bacteroides fragilis* phages.

11. The method according to claim 10 wherein the primer set is specific for an FRNA bacteriophage or group of related FRNA bacteriophages.

12. The method according to claim 8 wherein the virus is from a family selected from the group consisting of Adenoviridae, Caliciviridae, Picornaviridae, Hepadnaviridae, Flaviviridae, Reoviridae, Parvoviridae, Myoviridae, Podoviridae, Siphoviridae, Leviviridae, Inoviridae and Microviridae.

13. The method according to claim 8 wherein the anionic resin bead is a polystyrene spherical bead with a quaternary amine functional group.

14. The method according to claim 8 wherein the beads consist of anionic resin beads employing a functional group selected from the group consisting of quaternary amine, tertiary amine, and secondary amine.

15. The method according to claim 8 wherein the beads are suspended by an action selected from the group consisting of stirring; inversion and agitation.

16. A method of isolating and detecting a virus from a liquid comprising the steps of:

providing a liquid or liquefied homogenized food to be processed for virus isolation and detection;

suspending anionic resin beads having a diameter of about 0.49 mm or larger within the liquid or liquefied homogenized food;

sedimenting the anionic resin beads under atmospheric gravity;

separating the anionic resin beads from the liquid or liquefied homogenized food; and screening the anionic resin beads for the presence of a virus using a PCR-based technique.

17. The method according to claim 16 wherein the anionic resin bead is a polystyrene spherical bead with a quaternary amine functional group.

18. The method according to claim 16 wherein the anionic resin beads are screened for the presence of a bacteriophage.

19. The method according to claim 8 where the liquid is selected from the group consisting of environmental water samples, drinking water, milk, juice and homogenized foods.

20. The method according to claim 8 wherein the anionic resin beads are not subjected to a wash step after separating the beads from the liquid prior to the screening step.

21. The method according to claim 1 wherein the bead has a diameter of about 0.5 mm.

22. The method according to claim 1 wherein the bead consists essentially of an anion exchange resin.

23. The method according to claim 1 wherein volume of liquid is between about 0.50 liters and 60 liters.

* * * * *

UNITED STATES PATENT AND TRADEMARK OFFICE
CERTIFICATE OF CORRECTION

PATENT NO. : 10,072,307 B1
APPLICATION NO. : 12/693139
DATED : September 11, 2018
INVENTOR(S) : Lawrence D. Goodridge It is certified that error appears in the above-identified patent and that said Letters Patent is hereby corrected as shown below:

In the Claims

Column 16, Claim 3, Line 42 should read:
enzyme linked immunosorbent assay (ELISA), polymerase Signed and Sealed this
Fourteenth Day of May, 2019

Andrei Iancu
*Director of the United States Patent and Trademark Office*